United States Patent [19]

Maurer et al.

[11] 4,233,294
[45] Nov. 11, 1980

[54] METHOD OF COMBATTING PLUTELLA MACULIPENNIS WITH O-ISOPROPYL-S-[5-BROMO-PYRIMIDIN-2-YL]-THIONOTHIOL-METHANE-PHOSPHONIC ACID

[75] Inventors: Fritz Maurer, Wuppertal; Ingeborg Hammann, Cologne; Wolfgang Behrenz, Overath, all of Fed. Rep. of Germany

[73] Assignee: Bayer Aktiengesellschaft, Leverkusen, Fed. Rep. of Germany

[21] Appl. No.: 971,780

[22] Filed: Dec. 21, 1978

[30] Foreign Application Priority Data

Jan. 14, 1978 [DE] Fed. Rep. of Germany ....... 2801584

[51] Int. Cl.³ .................. A01N 57/16; C07F 9/65
[52] U.S. Cl. ................................ 424/200; 544/243
[58] Field of Search .................. 424/200; 544/243

[56] References Cited
U.S. PATENT DOCUMENTS

| | | | |
|---|---|---|---|
| 3,328,405 | 6/1967 | Simone et al. | 544/243 |
| 3,823,235 | 7/1974 | Haubein | 424/200 |
| 3,981,993 | 9/1976 | Maurer et al. | 424/200 |
| 4,014,996 | 3/1977 | Maurer et al. | 424/200 |
| 4,093,718 | 6/1978 | Maurer et al. | 424/200 |

Primary Examiner—Donald G. Daus
Assistant Examiner—Diana G. Rivers
Attorney, Agent, or Firm—Sprung, Felfe, Horn, Lynch & Kramer

[57] ABSTRACT

O-Alkyl-5-halo-pyrimidin-2-yl-thionothiol-phosphoric (phosphonic) acid esters of the formula

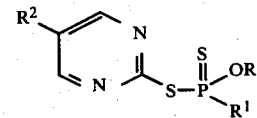

in which
R is alkyl,
R¹ is alkyl, aryl or alkoxy, and
R² is halogen,
which possess arthropodical properties.

1 Claim, No Drawings

METHOD OF COMBATTING PLUTELLA MACULIPENNIS WITH O-ISOPROPYL-S-[5-BROMO-PYRIMIDIN-2-YL]-THIONOTHIOL-METHANE-PHOSPHONIC ACID

The present invention relates to and has for its objects the provision of particular new O-alkyl-5-halo-pyrimidin-2-yl-thionothiol-phosphoric (phosphonic) acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that pyrimidinyl-thiono-thiolphosphoric acid esters, for example O,O-dimethyl- or O,O-diethyl-S-(2-chloro-4-methyl-pyrimidin-6-yl)-thionothiolphosphoric acid ester, have insecticidal properties (see German Auslegeschrift (German Published Specification) No. 1,445,709).

The present invention provides, as new compounds, the pyrimidin-2-yl-thiono-thiol-phosphoric (phosphonic) acid esters of the general formula

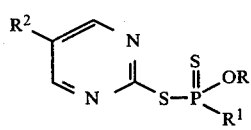

in which
R represents alkyl,
R¹ represents alkyl, aryl or alkoxy and
R² represents halogen.

Preferably, R represents straight-chain or branched alkyl with 1 to 6 (especially 1 to 4) carbon atoms, R¹ represents straight-chain or branched alkyl or alkoxy with, in either case, 1 to 6 (especially 1 to 4) carbon atoms or phenyl and R² represents chlorine or bromine.

Surprisingly, the pyrimidin-2-yl-thiono-thiol-phosphoric(phosphonic) acid esters according to the invention display a better insecticidal and acaricidal action than the corresponding compounds of analogous structure and the same type of action which are already known from the state of the art. The products according to the present invention thus represent a true enrichment of the art.

The invention also provides a process for the preparation of a pyrimidin-2-yl-thiono-thiol-phosphoric(phosphonic) acid ester of the formula (I) in which a thiono-thiol-phosphoric(phosphonic) acid ester of the general formula

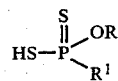

wherein R and R¹ have the meanings stated above, is reacted with a 2-chloro-pyrimidine of the general formula

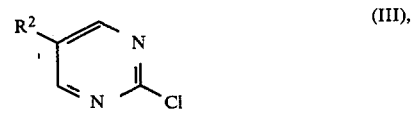

wherein R² has the meaning stated above, optionally in the presence of a solvent or diluent.

If, for example, O-methyl-thionothioletanephosphonic acid monoester and 2-chloro-5-bromo-pyrimidine are used as starting materials, the course of the reaction can be represented by the equation which follows:

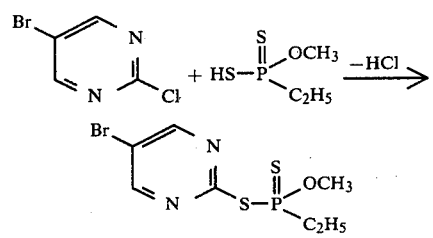

The thiono-thiol-phosphoric(phosphonic) acid esters (II) to be used as starting materials are known and also can be easily prepared industrially by processes which are known from the literature. Examples of these esters which may be mentioned are: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O,-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl and O-iso-propyl-O-butyl-thionothiolphosphoric acid diester, and O-methyl-, O-ethyl-, O-n-propyl-, O-iso-propyl-, O-n-butyl-, O-iso-butyl-, O-sec.-butyl- and O-tert.-butyl-methane- and -ethane-, -n-propane-, -iso-propane-, -n-butane-, -iso-butane-, -sec.-butane- and -benzene-thionothiolphosphonic acid monoester.

The 2-chloro-pyrimidines (III) which are also to be used as starting materials can be prepared, analogously to processes which are known from the literature, by reacting the corresponding 2-hydroxypyrimidines with inorganic acid chlorides, for example phosphorus oxychloride (compare Australian J. Chem. 17, (1964), 794–802).

Examples of these pyrimidines which may be mentioned are 2,5-dichloro-pyrimidine and 2-chloro-5-bromo-pyrimidine.

The process for the preparation of the pyrimidinyl-thiono-thiol-phosphoric(phosphonic) acid esters according to the invention is preferably carried out using a suitable solvent or diluent. Possible solvents and diluents are virtually all the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

The reaction temperature can be varied within a substantial range. In general, the reaction is carried out at from 0° to 100° C., preferably at 10° to 60° C.

In general, the reaction is allowed to proceed under normal pressure.

For carrying out the process according to the invention, the starting materials are employed in approximately equimolar amounts. It is equally well possible to employ the thiono-thiol-phosphoric(phosphonic) acid esters in an excess of up to about 30 mol percent, preferably up to about 10 mol percent.

The thiono-thiol-phosphoric(phosphonic) acid esters are optionally liberated from their alkali metal salts in situ (i.e. without intermediate isolation) by adding an at least equimolar amount of an acid, such as hydrochloric acid or sulphuric acid.

The reaction is preferably carried out in one of the solvents or diluents indicated above, in the temperature range given. After a reaction time of one or more hours, the reaction solution is appropriately washed with aqueous carbonate solution or bicarbonate solution and worked up in the customary manner by drying the organic phase and evaporating off the solvent.

Some of the new compounds are obtained in the crystalline form and others are obtained in the form of oils. The latter cannot be distilled without decomposition, but can be freed from volatile constituents by so-called "incipient distillation," that is to say by prolonged heating to moderately elevated temperatures under reduced pressure, and can be purified in this manner. The melting point or the refractive index are used for characterizing the new compounds.

Particularly preferred compounds of formula (I) which may be mentioned are: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-S-[5-chloro-pyrimidin-2-yl]-dithiophosphoric acid ester; O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-S-[5-bromopyrimidin-2-yl]-dithiophosphoric acid ester; O-methyl-, O-ethyl-, O-n-propyl-, O-iso-propyl-, O-n-butyl-, O-iso-butyl-, O-sec.-butyl- and O-tert.-butyl-S-[5-chloropyrimidin-2-yl]-methanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-methanedithiophosphonic acid ester; O-methyl-, O-ethyl-, O-n-propyl-, O-iso-propyl-, O-n-butyl-, O-iso-butyl-, O-sec.-butyl and O-tert.-butyl-S-[5-chloropyrimidin-2-yl]-ethanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-ethanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-chloropyrimidin-2-yl]-n-propanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-n-propanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-chloropyrimidin-2-yl]-iso-propanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-iso-propanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-chloropyrimidin-2-yl]-n-butanedithiophosphonic acid ester; O-methyl-, O-ethyl-, O-n-propyl-, O-iso-propyl-, O-butyl-, O-iso-butyl-, O-sec.-butyl- and O-tert.-butyl-S-[5-bromopyrimidin-2-yl]-n-butanedithiophosphonic acid ester; O-methyl-, O-ethyl-, O-n-propyl, O-iso-propyl-, O-n-butyl-, O-iso-butyl-, O-sec.-butyl- and O-tert.-butyl-S-[5-chloropyrimidin-2-yl]-iso-butanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-iso-butanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-chloropyrimidin-2-yl]-sec.-butanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-sec.-butanedithiophosphonic acid ester; O-methyl-, O-ethyl-, O-n-propyl-, O-iso-propyl-, O-n-butyl-, O-iso-butyl-, O-sec.-butyl- and O-tert.-butyl-S-[5-chloropyrimidin-2-yl]-benzenedithiophosphonic acid ester; and O-methyl-, O-ethyl-, O-n-propyl-, O-iso-propyl-, O-n-butyl-, O-iso-butyl-, O-sec.-butyl- and O-tert.-butyl-S-[5-bromopyrimidin-2-yl]-benzenedithiophosphonic acid ester.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolantha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Mesca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Zenopsylla cheopis* and Ceratophyllus spp.;

from the class of the Arachnida, for example Scorpio maurus and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combatting arthropods, especially insects and acarids, which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The invention will be further described in the following illustrative examples:

EXAMPLE 1

(a) The 2-chloro-5-halogenopyrimidines to be employed as starting materials could be prepared, for example, as follows:

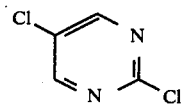

A mixture of 131 g (1 mol) of 2-hydroxy-5-chloropyrimidine [for the preparation see L. A. Paquette and W. C. Farley, J. Org. Chem. 32 (1967) page 2,725] and 400 ml of phosphorous oxychloride was boiled under reflux for 3 hours. The mixture was then evaporated in vacuo, the residue was poured onto ice and the mixture was extracted by shaking twice with 300 ml of methylene chloride each time. The organic phases were dried over sodium sulphate and the solvent was then distilled off in vacuo. 73 g (49% of theory) of 2,5-dichloropyrimidine remained, with the melting point 51° C.

The following compound was prepared in an analogous manner:

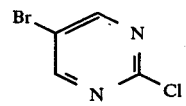

in a yield of 77% (of theory) and with the melting point 77° C.

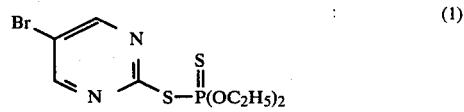

A mixture of 9.7 g (0.05 mol) of 2-chloro-5-bromopyrimidine, 9.3 g (0.05 mol) of O,O-diethyldithiophosphoric acid diester and 100 ml of acetone was stirred at 45° C. for 12 hours. 200 ml of toluene were then added and the mixture was extracted by shaking twice with dilute sodium bicarbonate solution. The organic phase was dried over sodium sulphate and evaporated in vacuo. The residue was subjected to incipient distillation. 12 g (70% of theory), of O,O-diethyl-S-[5-bromo-pyrimidin-2-yl]-thionothiolphosphoric acid ester were thus obtained in the form of a yellow oil having a refractive index $n_D^{21}$ of 1.5979.

EXAMPLE 2

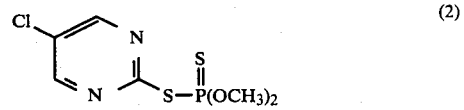

A mixture of 10 ml of concentrated hydrochloric acid and 20 g of ice was added all at once to a mixture of 14.9 g (0.2 mol) of 2,5-dichloropyrimidine, 21.6 g (0.11 mol) of the potassium salt of O,O-dimethyldithiophosphoric acid diester, 150 ml of toluene and 50 ml of water. The mixture was subsequently stirred at room temperature for 24 hours, the aqueous phase was separated off and the organic phase was extracted by shaking once with potassium carbonate solution and once again with water. The organic phase was dried over sodium sulphate and evaporated in vacuo. The residue was triturated with petroleum ether and, after crystallization, the product was filtered off. 18 g (67% of theory) of O,O-dimethyl-S-[5-chloropyrimidin-2-yl]-thionothiolphosphoric acid ester were thus obtained in the form of pale yellow crystals with the melting point 54° C.

The following compounds of the general formula

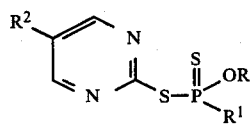

could be prepared analogously:

| Compound No. | R | R$^1$ | R$^2$ | Yield (% of theory) | Physical data (refractive index; melting point °C.) |
| --- | --- | --- | --- | --- | --- |
| 3 | CH$_3$ | OCH$_3$ | Br | 54 | 63 |
| 4 | C$_3$H$_7$-iso | CH$_3$ | Br | 43 | 59 |
| 5 | C$_2$H$_5$ | C$_2$H$_5$ | Br | 55 | $n_D^{24}$: 1.6186 |
| 6 | CH$_3$ | C$_2$H$_5$ | Br | 48 | $n_D^{24}$: 1.6366 |
| 7 | C$_2$H$_5$ | ⟨phenyl⟩ | Br | 24 | $n_D^{22}$: 1.6534 |
| 8 | C$_2$H$_5$ | OC$_2$H$_5$ | Cl | 70 | $n_D^{23}$: 1.5728 |
| 9 | C$_2$H$_5$ | C$_2$H$_5$ | Cl | 73 | $n_D^{23}$: 1.5980 |
| 10 | CH$_3$ | C$_2$H$_5$ | Cl | 71 | $n_D^{23}$: 1.6150 |
| 11 | C$_3$H$_7$-iso | CH$_3$ | Cl | 39 | 68 |
| 12 | C$_2$H$_5$ | CH$_3$ | Cl | | |
| 13 | C$_2$H$_5$ | OC$_3$H$_7$-n | Cl | | |

The activity of the compounds of this invention is illustrated by the following examples wherein the compounds according to the present invention are each identified by the number (given in brackets) from the preparative examples hereinabove:

EXAMPLE 3

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all of the flies were killed; 0% meant that none of the flies were killed.

In this test, for example, the following compounds showed a superior activity compared to the prior art: (1), (2), (3), (4), (5), (6), (8), (9), (10) and (11).

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (1), (2), (3), (4), (5), (6), (8), (9), (10) and (11).

EXAMPLE 5

LT$_{100}$ test for Diptera
Test insects: *Aedes aegypti*
Number of test insects: 20
Solvent: acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

In this test, for example, the following compounds showed a superior action compared to the prior art: (1), (2), (3), (4), (5), (8), (9) and (10).

It will be appreciated that the instant specification and examples are set forth by way of illustration and not limitation, and that various modifications and changes may be made without departing from the spirit and scope of the present invention.

What is claimed is:

1. A method of combating Plutella maculipennis which comprises applying thereto or to a habitat thereof an arthropodicidally effective amount of O-isopropyl-S-[5-bromo-pyrimidin-2-yl]-thionothiolmethane-phosphonic acid ester of the formula

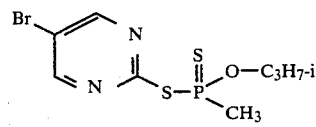

* * * * *